US008231746B1

(12) United States Patent
Bellitto (10) Patent No.: US 8,231,746 B1
(45) Date of Patent: Jul. 31, 2012

(54) METHOD AND DEVICE FOR DETECTION OF A NITROAROMATIC EXPLOSIVE (75) Inventor: Victor J. Bellitto, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1099 days.

(21) Appl. No.: 12/214,295

(22) Filed: May 28, 2008

(51) Int. Cl.
C06B 45/00 (2006.01)
C06B 45/18 (2006.01)
C06B 45/32 (2006.01)
C06B 25/00 (2006.01)
C06B 25/04 (2006.01)
D03D 23/00 (2006.01)
D03D 43/00 (2006.01)

(52) U.S. Cl. ....... 149/3; 149/2; 149/6; 149/88; 149/105; 149/108.4; 149/109.6

(58) Field of Classification Search .................. 149/2, 3, 149/6, 88, 105, 108.4, 109.6
See application file for complete search history.

(56) References Cited

U.S. PATENT DOCUMENTS

| | | | | |
|---|---|---|---|---|
| 7,171,312 | B2* | 1/2007 | Steinthal et al. | 702/32 |
| 7,295,019 | B2* | 11/2007 | Yang et al. | 324/663 |
| 2004/0234958 | A1* | 11/2004 | Smith et al. | 435/6 |
| 2006/0176062 | A1* | 8/2006 | Yang et al. | 324/663 |
| 2007/0113642 | A1* | 5/2007 | Bonne et al. | 73/204.11 |
| 2009/0275143 | A1* | 11/2009 | Misra et al. | 436/130 |

OTHER PUBLICATIONS

Yinon, J., Detection of Explosives by Electronic Noses, Anal. Chem. Mar. 1, 2003, 99-105 A.
S.R. Waker, W.M. Koppes. Venom Penetrator Chem Mine Neutralization National Defense Industrial Association, Proceedings of the 2005 Warheads & Ballistics Symposium. CA. Aug. 2005.
D.M. Rosenberg, W.M Koppes, K.A. Clark, M.E. Sitzmann, B.E. Vos, P.Politzer, J.S. Murray, Chem Neutralization of nitroarene-based energetic mixtures: Optimization of the hypergolic reaction with amines based on a structure/reactivity study. 230th American Chem Society National Meeting, Washington, D.C. Aug.-Sep. 2005.
A.V. Mamishev, K. Sundara-Rajan, F. Yang, Y. Du, and M. Zahn, Interdigital Sensors and Transducers, Proceedings of the IEEE. vol. 92, No. 5. May 2004, 808-845.
Guirguis, R., "Chemical Ignition of Explosives Using Pyrotechnics and Hypergolics," Proceedings of the 12th International Detonation Symposium, held in Norfolk, VA, Jul. 2006.

* cited by examiner

Primary Examiner — James McDonough
(74) Attorney, Agent, or Firm — Fredric J. Zimmerman (57) ABSTRACT

Detecting a nitroaromatic explosive via an exothermic chemical reaction of the nitroaromatic explosive with a polyamine or polyamine functional group is accomplished by depositing a polyamine or polyamine-functionalized coating on a microelectrode array and a semiconductor substrate, introducing a nitroaromatic explosive to an exposed surface of the polyamine or polyamine-functionalized coating, and measuring changes in electrical properties of the polyamine or polyamine-functionalized coating associated with the introducing of the nitroaromatic explosive. The nitroaromatic explosive detector comprises a microelectrode array formed on a semiconductor substrate, a polyamine or polyamine-functionalized coating deposited on and contiguous with the microelectrode array and the semiconductor substrate, and a measuring device for measuring any of resistance, conductance, and capacitance across the microelectrode array.

16 Claims, 8 Drawing Sheets

METHOD AND DEVICE FOR DETECTION OF A NITROAROMATIC EXPLOSIVE

STATEMENT OF GOVERNMENT INTERESTS

The invention described herein may be manufactured and used for the Government of the United States of America for governmental purposes without payment of any royalties thereon or therefore.

FIELD OF THE INVENTION

The present invention generally relates to a method and device that may detect a nitroaromatic explosive via an exothermic chemical reaction of the nitroaromatic explosive with a polyamine or a polyamine-functionalized coating of a sensor's surface. Particularly, the detection of the exothermic reaction between a nitroaromatic explosive molecule and a polyamine molecule or polyamine functional group may alter electrical properties of the polyamine or polyamine-functionalized coating.

BACKGROUND OF THE INVENTION

Police and military forces throughout the world are confronted with the problem of detecting explosives. Optimally, detection of explosives could occur at a distance by sampling volatiles in the air for explosives.

Several types of chemo-electronic sensors are currently used to detect explosives. Fluorescent polymers that react to volatile chemicals, such as nitrogen-containing compounds from explosives, can detect trinitrotoluene (TNT) in the femtogram range by measuring increases or decreases in fluorescence when the explosive interacts with the fluorescent polymer. Sensor arrays, comprising thousands of microsphere sensors, each responding to a particular chemical compound or class of compounds by fluorescing at different wavelengths, can detect TNT and 2,4-dinitrotoluene (2,4-DNT) in the low parts per billion range. An array of different polymeric thin film sensors, which responds to numerous chemical compounds to produce a pattern of electrical resistance changes analyzed by a neural network, can detect 2,4-DNT at a level of about 0.2 parts per billion. A chemiresistor vapor sensor, based on semiconducting films of alkanethiol-stabilized gold nanoclusters deposited on an interdigitated microelectrode array, can measure changes in electrical conductivity when exposed to vapors of dinitrobenzene, 2,4-DNT, and TNT at room temperature. A surface acoustic wave (SAW)-based gas chromatograph can detect 2,4-DNT at an estimated limit of 92 parts per trillion.

Greater sensitivity than that achieved by the explosive detectors outlined above would allow detection of explosives at a greater distance, explosives with a low vapor pressure, explosives packed in a container, for example, land mines or improvised explosive devices (IEDs), and the reduction of false positive detections. There exists a requirement for the sensitivity of explosive detectors to detect a cluster of molecules or even a single molecule. In the above explosive detectors, however, the inability to detect the interaction of single explosive molecule with a sensing molecule, that is, a single binding event, is due to their inability to provide an adequate method of amplification. Typically, electronic amplification is inadequate because of the poor signal-to-noise ratio.

Figure 1:
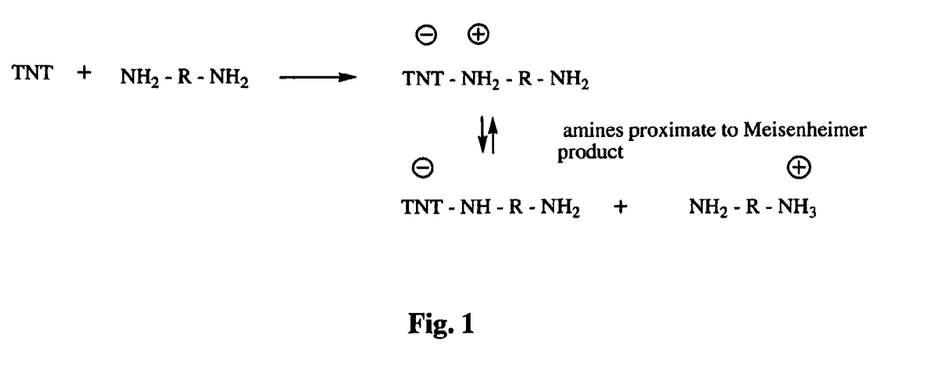
FIG. 1 (Background) illustrates a reaction between trinitrotoluene (TNT), a nitroaromatic explosive, and a polyamine to form a zwitterionic Meisenheimer complex having a labile proton.
Figure 2:
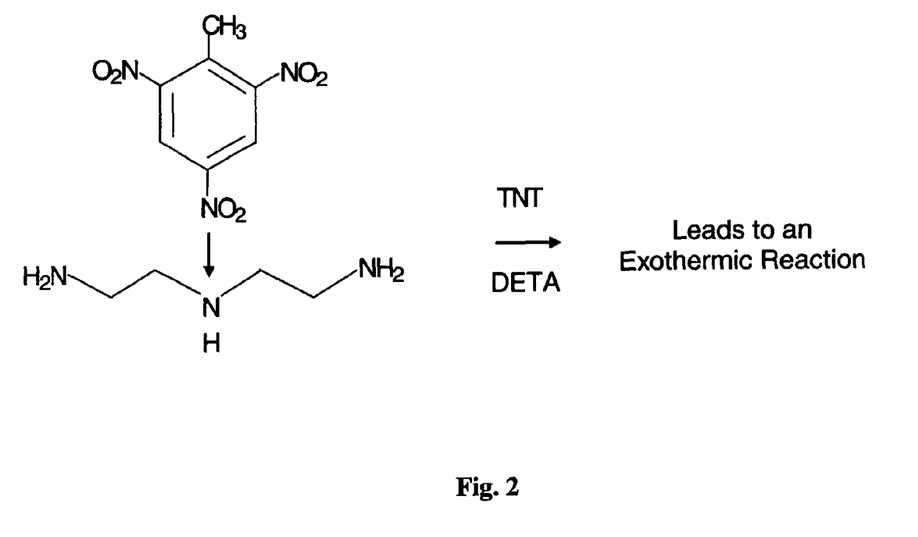
FIG. 2 (Background) illustrates an exothermic reaction between trinitrotoluene (TNT), a nitroaromatic explosive, and diethylenetriamine (DETA)

Recent research (D. M. Rosenberg et al., "Chemical neutralization of nitroarene-based energetic mixtures: Optimization of the hypergolic reaction with amines based on a structure/reactivity study", 230th American Chemical Society National Meeting, Washington, D.C., Aug. 28-Sep. 1, 2005), indicates that a nitroarene explosive molecule, for example, 2,4-DNT or TNT, reacts with a polyamine molecule, for example, diethylenetriamine (DETA), in an irreversible capture by means of covalent bond formation. As shown in FIG. 1, the reaction product formed is a zwitterionic Meisenheimer complex having a labile proton. Given the exothermic nature of the reaction between the nitroarene explosive and the polyamine, as shown in FIG. 2, the resulting increase in kinetic energy imparted to the region of proton exchange about the nitroarene point of attachment, may induce greater and/or more rapid separation of electrical charges.

Figure 3:
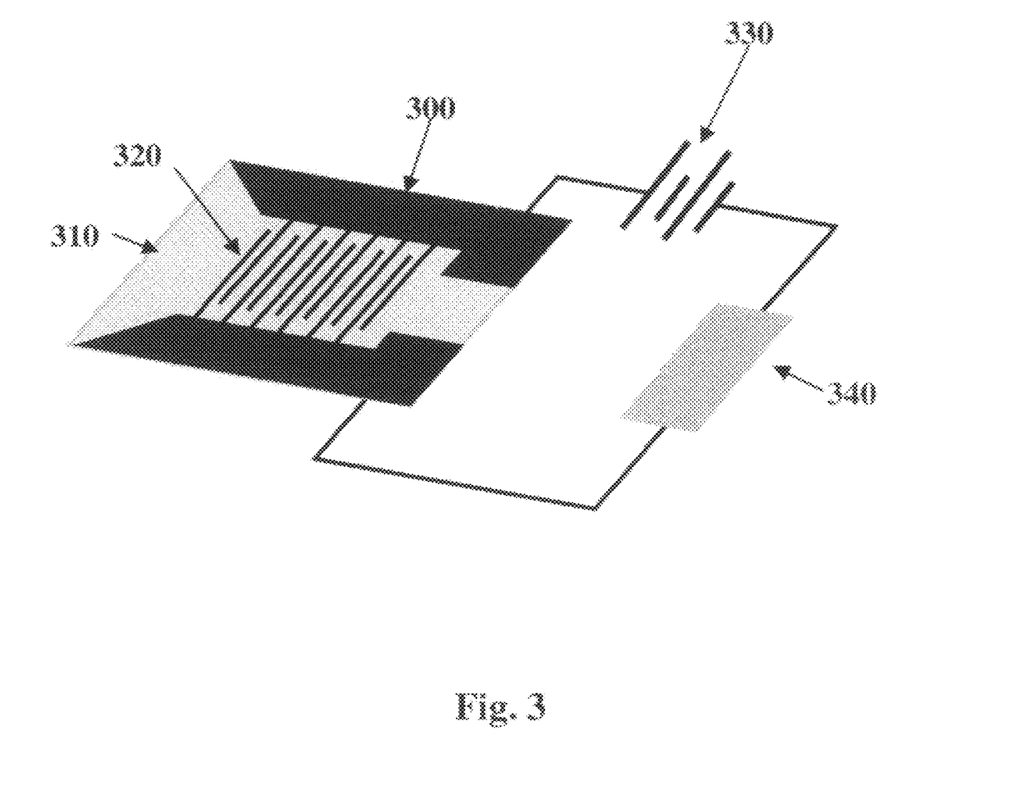
FIG. 3 (Background) illustrates an interdigital microelectronic array.

As shown in FIG. 3, the effect of adsorbed vapors on the electrical properties of thin films is often studied with a microelectrode array. Although FIG. 3 illustrates a periodic interdigital microelectrode array, that is, an array where the distance between the microelectrodes is a constant, non-periodic microelectrode arrays are also used. Other geometries of microelectrode arrays, for example, concentric annular arrays, are also used to study the electrical properties of thin films.

The interdigitating microelectrodes, shown in FIG. 3, are formed on a semiconductor substrate by well known semiconductor technology methods. A thin film of the material under study is deposited over the microelectrode array and the semiconductor substrate. The underlying interdigital microelectrode array forms the equivalent of a parallel capacitor array, where electrical-field fringe effects penetrate the overlying thin film of the material under study. When vapors are adsorbed on the upper surface of the thin film, changes to the electrical properties, for example, resistance, conductance, and capacitance, of the thin film are measured across the electrodes. Time-varying currents and voltages can be applied to the electrodes, as is well known in the art, to facilitate the measurement of the electrical characteristics of the thin film.

Microelectrode arrays are small, inexpensive, rugged, and offer a well known method for studying changes in electrical characteristics of a thin film of a material under study, when vapors are adsorbed by the thin film.

There remains a need for an explosive detector that may be small, inexpensive and rugged, and that may detect a cluster of molecules or even a single molecule of an explosive.

SUMMARY OF THE INVENTION

An exemplary aspect of the present invention uses an exothermic chemical reaction between a nitroaromatic explosive and a polyamine to provide chemical "amplification" of a binding event between a nitroaromatic explosive molecule and a polyamine molecule or polyamine functional group, which is part of a coating of an explosive detector's sensor surface. When a nitroaromatic explosive molecule, for example, 2,4-DNT or TNT, irreversibly reacts with a polyamine molecule or polyamine-functional group, for example, diethylenetriamine (DETA), a zwitterionic Meisenheimer complex is formed that has a labile proton. The exothermic nature of the reaction may result in an increase in kinetic energy imparted to the region of proton exchange about the nitroaromatic point of attachment. When the polyamine molecule or polyamine function group comprises part of a coating of a microelectrode array and a semiconductor substrate, the greater and/or more rapid separation of electrical charges produced by the exothermic reaction with the nitroaromatic explosive molecule may produce a much larger change to the electrical characteristics of the polyamine or polyamine functionalized coating. The polyamine or polyamine functionalized coating can adhere to the semiconductor substrate or to the microelectrode array and the semiconductor substrate. Therefore, the change in electrical characteristics of the polyamine or polyamine functionalized coating to the adsorption of the nitroaromatic molecule are chemically "amplified" by the exothermic reaction, which produces greater and/or more rapid separation of electrical charges about the region of proton exchange associated with the point of nitroaromatic attachment to the polyamine molecule or polyamine functional group.

An exemplary embodiment of the present invention includes a method for detecting a nitroaromatic explosive comprising: forming a microelectrode array on a semiconductor substrate; depositing a polyamine or polyamine functionalized coating on the microelectrode array and the semiconductor substrate; introducing a nitroaromatic explosive to an exposed surface of the polyamine or polyamine functionalized coating; and measuring changes in electrical properties of the polyamine or polyamine functionalized coating associated with the introducing the nitroaromatic explosive, in which a chemical reaction between a polyamine molecule or polyamine functional group of the polyamine or polyamine functionalized coating and a nitroaromatic molecule of the nitroaromatic explosive is exothermic.

Another exemplary embodiment of the present invention includes the method for detecting a nitroaromatic explosive, in which the depositing of the polyamine or polyamine-functionalized coating on the microelectrode and the semiconductor substrate comprises vapor deposition of the polyamine or polyamine-functionalized coating.

Yet another exemplary embodiment of the present invention includes the method for detecting a nitroaromatic explosive, in which the depositing of the polyamine-functionalized coating on the microelectrode array and the semiconductor substrate comprises depositing a polyamine-functionalized silica-gel.

Yet another exemplary embodiment of the present invention includes the method for detecting a nitroaromatic explosive, in which the polyamine coating comprises any of diethylenetriamine (DETA), N-(3-aminopropyl)-1,3-propanediamine, ethylenediamine, 1,3-diaminopropane, 1,4-diaminobutane, 1,5-diaminopentane, 1,12-dodecanediamine (Spermine), hexamethylenediamine, bis(hexamethylene)triamine, N,N'-diethylethylenediamine, tris(2-aminoethyl)amine, N,N-diethylethylenediamine, diethylenetriaminepentaacetate (DTPA), [3-(2-aminoethylamino)propyl]trimethoxysilane, and 3-[2-(2-aminoethylamino)ethylamino]propyl-trimethoxysilane.

Yet another exemplary embodiment of the present invention includes the method for detecting a nitroaromatic explosive, in which the polyamine-functionalized coating comprises any of 3-(diethylenetriamino)propyl-functionalized silica, 3-(ethylenediamino)propyl-functionalized silica, and 3-aminopropyl-functionalized silica.

Yet another exemplary embodiment of the present invention includes the method for detecting a nitroaromatic explosive, in which the introducing of a nitroaromatic explosive comprises any of 2,4-dinitrotoluene (2,4-DNT), 2-methyl-1,3,5-trinitrobenzene (TNT), 2,4,6-trinitrophenyl-N-methlynitramine (Tetryl), 1,3,5-trinitro-2-[2-(2,4,6-trinitrophenyl)ethenyl]benzene (HNS), 2,4,6-trinitrophenol (picric acid) and its salts, 1,3,5-triazido-2,4,6-trinitrobenzene (TNB), 1,3,5-triamino-2,4,6-trinitrobenzene (TATB), 2,4,6-trinitroaniline (TNA), 2,4,6 trinitro-1,3 benzenediamine (DATB), and 2-diazo-4,6-dinitrophenol (DDNP).

Yet another exemplary embodiment of the present invention includes the method for detecting a nitroaromatic explosive, in which the measuring changes in electrical properties of the polyamine or polyamine-functionalized coating comprises measuring any of resistance, conductance, and capacitance across the microelectrode array.

Yet another exemplary embodiment of the present invention includes a nitroaromatic explosive detector comprising: a microelectrode array formed on a semiconductor substrate; a polyamine or polyamine functionalized coating deposited on and contiguous with the microelectrode array and the semiconductor substrate, in which the polyamine or polyamine functionalized coating includes an exposed surface upon which the nitroaromatic explosive is adsorbed; and a measuring device for measuring any of resistance, conductance, and capacitance across the microelectrode array to detect the nitroaromatic explosive, in which a chemical reaction between a polyamine molecule or polyamine functional group of the polyamine or polyamine functionalized coating and an explosive nitroaromatic molecule is exothermic.

Yet another exemplary embodiment of the present invention includes the nitroaromatic explosive detector, in which the polyamine or polyamine functionalized coating on the microelectrode array and the semiconductor substrate is vapor deposited to a thickness from about 1 nm to about 100,000 nm.

Yet another exemplary embodiment of the present invention includes the nitroaromatic explosive detector, in which the polyamine-functionalized coating on the microelectrode array and the semiconductor substrate comprises a polyamine-functionalized silica-gel deposited to a thickness from about 1 nm to about 100,000 nm.

Yet another exemplary embodiment of the present invention includes the nitroaromatic explosive detector, in which the polyamine coating comprises any of diethylenetriamine (DETA), N-(3-aminopropyl)-1,3-propanediamine, ethylenediamine, 1,3-diaminopropane, 1,4-diaminobutane, 1,5-diaminopentane, 1,12-dodecanediamine (Spermine), hexamethylenediamine, bis(hexamethylene)triamine, N,N'-diethylethylenediamine, tris(2-aminoethyl)amine, N,N-diethylethylenediamine, diethylenetriaminepentaacetate (DTPA), [3-(2-aminoethylamino)propyl]trimethoxysilane, and 3-[2-(2-aminoethylamino)ethylamino]propyl-trimethoxysilane.

Yet another exemplary embodiment of the present invention includes the nitroaromatic explosive detector, in which the polyamine-functionalized coating comprises any of 3-(diethylenetriamino)propyl-functionalized silica, 3-(ethylenediamino)propyl-functionalized silica, and 3-aminopropyl-functionalized silica.

Yet another exemplary embodiment of the present invention includes the nitroaromatic explosive detector, in which the nitroaromatic explosive comprises any of 2,4-dinitrotoluene (2,4-DNT), 2-methyl-1,3,5-trinitrobenzene (TNT), 2,4,6-trinitrophenyl-N-methlynitramine (Tetryl), 1,3,5-trinitro-2-[2-(2,4,6-trinitrophenyl)ethenyl]benzene (HNS), 2,4,6-trinitrophenol (picric acid) and its salts, 1,3,5-triazido-2,4,6-trinitrobenzene (TNB), 1,3,5-triamino-2,4,6-trinitrobenzene (TATB), 2,4,6-trinitroaniline (TNA), 2,4,6 trinitro-1,3 benzenediamine (DATB), and 2-diazo-4,6-Dinitrophenol (DDNP).

Yet another exemplary embodiment of the present invention includes the nitroaromatic explosive detector, in which the microelectrode array comprises any of silver, gold, platinum, palladium, nickel, chromium, copper, iron, tungsten, titanium, zinc, manganese, tantalum, and aluminum.

Yet another exemplary embodiment of the present invention includes the nitroaromatic explosive detector, in which the semiconductor substrate comprises any of silicon, indium nitride, silicon dioxide, germanium, gallium arsenide, gallium nitride, silicon carbide, and silicon nitride.

Yet another exemplary embodiment of the present invention includes the nitroaromatic explosive detector, in which the measuring device for measuring any of resistance, conductance, and capacitance further comprises a direct current power supply and a time-varying power supply.

BRIEF DESCRIPTION OF THE DRAWINGS

Exemplary embodiments of the present invention are discussed hereinafter in reference to the drawings, in which:

FIG. 4 A depicts a photomicrograph of an atomic force microscope (AFM) image of a bare microelectrode array surface including bare silicon dioxide and bare gold surfaces;

FIG. 4 B depicts an AFM image of trimethoxysilyl-ethylenediamine adsorbed on the silicon dioxide section of the microelectrode array's and substrate's surface in an exemplary embodiment of the present invention;

FIG. 4 C depicts an AFM image of 3-aminopropyl functionalized silica gel adsorbed on the silicon dioxide and gold surfaces of the microelectrode array's and substrate's surfaces in an exemplary embodiment of the present invention;

DETAILED DESCRIPTION OF EXEMPLARY EMBODIMENTS OF THE INVENTION

An exemplary embodiment of the present invention may include a nitroaromatic explosive detector comprising a microelectrode array, and a polyamine or polyamine-functionalized coating that is contiguous with and overlies the microelectrode array, in which a single binding event between a nitroaromatic molecule and a polyamine molecule produces an exothermic reaction. Specifically, the nitroaromatic explosives that may be detected include 2,4-dinitrotoluene (2,4-DNT), 2-methyl-1,3,5-trinitrobenzene (TNT), 2,4,6-trinitrophenyl-N-methlynitramine (Tetryl), 1,3,5-trinitro-2-[2-(2,4,6-trinitrophenyl)ethenyl]benzene (HNS), 2,4,6-trinitrophenol (picric acid) and its salts, 1,3,5-triazido-2,4,6-trinitrobenzene (TNB), 1,3,5-triamino-2,4,6-trinitrobenzene (TAM), 2,4,6-trinitroaniline (TNA), 2,4,6 trinitro-1,3 benzenediamine (DATB), 2-diazo-4,6-dinitrophenol (DDNP). The polyamines that comprise the polyamine coating may include diethylenetriamine (DETA), N-(3-aminopropyl)-1,3-propanediamine, ethylenediamine, 1,3-diaminopropane, 1,4-diaminobutane, 1,5-diaminopentane, 1,12-dodecanediamine (Spermine), hexamethylenediamine, bis(hexamethylene)triamine, N,N'-diethylethylenediamine, tris(2-aminoethyl)amine, and N,N-diethylethylenediamine, diethylenetriaminepentaacetate (DTPA), [3-(2-Aminoethylamino)propyl]trimethoxysilane, and 3-[2-(2-Aminoethylamino)ethylamino]propyl-trimethoxysilane.

The polyamine coating may optionally comprise a polyamine-functionalized silica gel, for example, 3-(diethylenetriamino)propyl-functionalized silica, 3-(ethylenediamino)propyl-functionalized silica, and 3-aminopropyl-functionalized silica.

Although FIG. 3 illustrates a periodic interdigital microelectrode array, the explosive detector of an exemplary embodiment of the present invention may include other geometries of microelectrode arrays, for example, concentric annular microelectrode arrays, and non-periodic microelectrode arrays. The microelectrode array 300 of various exemplary embodiments of the present invention may be made by semiconductor technology methods well known in the art. The microelectrodes 320 of the microelectrode array may comprise any of silver, gold, platinum, palladium, nickel, chromium, copper, iron, tungsten, titanium, zinc, manganese, tantalum, and aluminum. The substrate 310 upon which the microelectrode array 300 is formed may comprise any of silicon, indium nitride, silicon dioxide, germanium, gallium arsenide, gallium nitride, silicon carbide and silicon nitride in various exemplary embodiments of the present invention.

Electrical measurements of resistance, conductance and/or capacitance (more correctly, transconductance and transcapacitance) across the microelectrode array may be accomplished by methods and structures 340 well known in the art. In various exemplary embodiments of the present invention, direct current power supplies 330 and/or time-varying power supplies may supply known currents and voltages to the microelectrode array.

The polyamine or polyamine functionalized coating may be applied to the microelectrode array in a conventional manner as a fluid or well known semiconductor deposition methods, for example, vapor deposition. The deposition method may utilize: an ultra high vacuum (less than about $10^{-9}$ Torr); a high vacuum (from about $10^{-6}$ to about $10^{-8}$ Torr); a medium vacuum (from about $10^{-3}$ to about $10^{-5}$ Torr); a low vacuum (from about 1 to about $10^{-3}$ Ton); an inert atmosphere, including, for example, any of argon, helium, and nitrogen; or a combination of a moderate vacuum with an inert atmosphere. The thickness of the deposited polyamine or polyamine functionalized coating may range from about 1 nanometer (nm) to about 100,000 nm.

Deposition of the polyamine or polyamine functionalized coating onto the microelectrode array may be accomplished in an ultra high vacuum (UHV) apparatus including a stainless steel UHV chamber with a working base pressure of $1\times10^{-10}$ Torr. The UHV chamber may contain, among other things, a hemispherical analyzer used in concert with a dual Al/Mg $K_\alpha$ X-ray source for X-ray photoelectron spectroscopy (XPS) to provide compositional analysis, a quadrupole mass spectrometer for residual gas analysis, a calibrated directed-flux doser, and ZnSe windows to transmit light for Fourier transform infrared (FTIR) spectroscopy to characterize surface bonding and polyamine orientation. Deposition thickness of the polyamine or polyamine functionalized coating may be monitored with a quartz crystal microbalance and may range from about 1 nm to about 1000 nm.

The polyamine or polyamine functionalized material may be introduced into the UHV chamber by differential pumping from a glass bulb. The glass bulb may be attached to the UHV chamber via a glass-to-metal seal. Regulation of the introduction of the polyamine or polyamine functionalized material may be accomplished by use of an all-metal Nupro valve and by heating of the glass bulb with an oil bath. Vapor deposition of the polyamine or polyamine functionalized material in the ultra high vacuum environment may prevent contamination of the energetic composition by $H_2O$, $O_2$, etc.

Alternatively, the polyamine coating may comprise a polyamine-functionalized silica gel, for example, a 3-aminopropyl functionalized silica gel, which is deposited on the surface of the microelectrode in a conventional manner as a fluid, a slurry, or a powder. Such polyamine-functionalized silica gels may range in thickness from about 1 nm to about 100,000 nm.

Figure 4A:
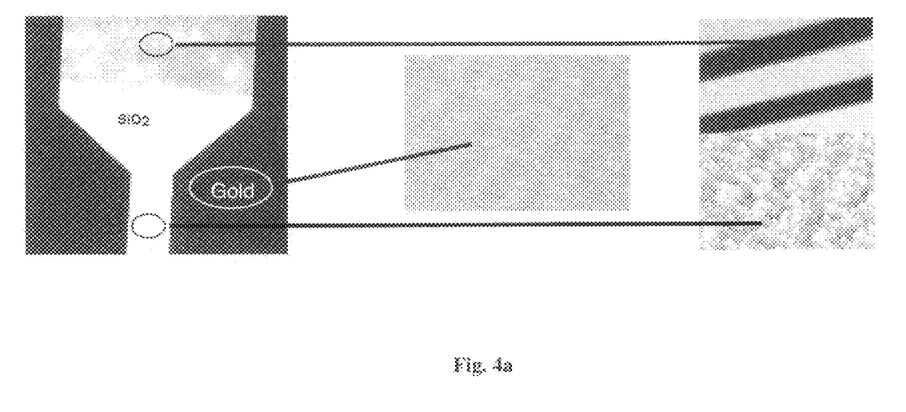
Figure 4B:
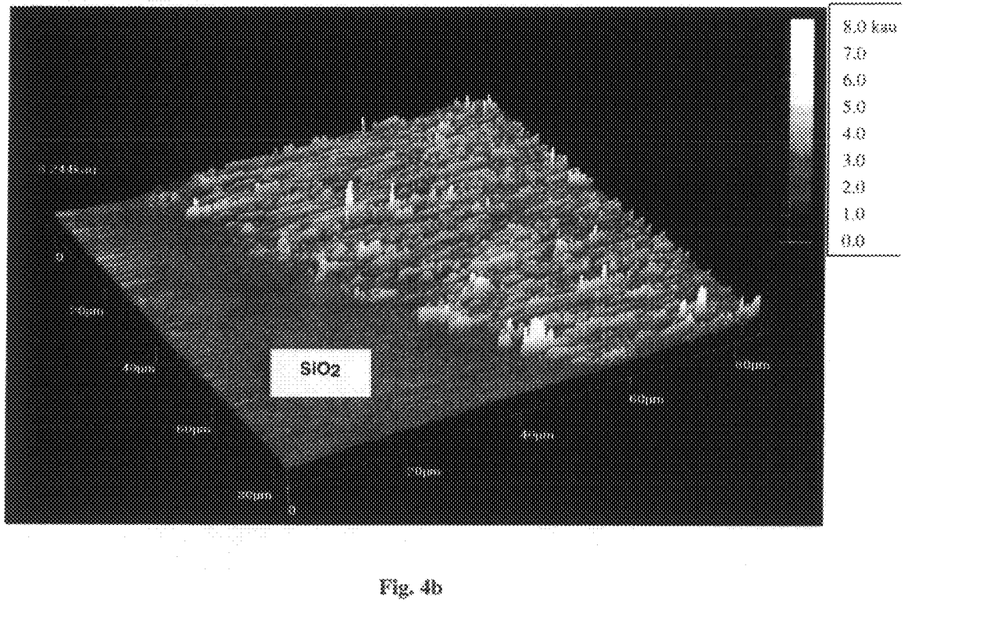
Figure 4C:
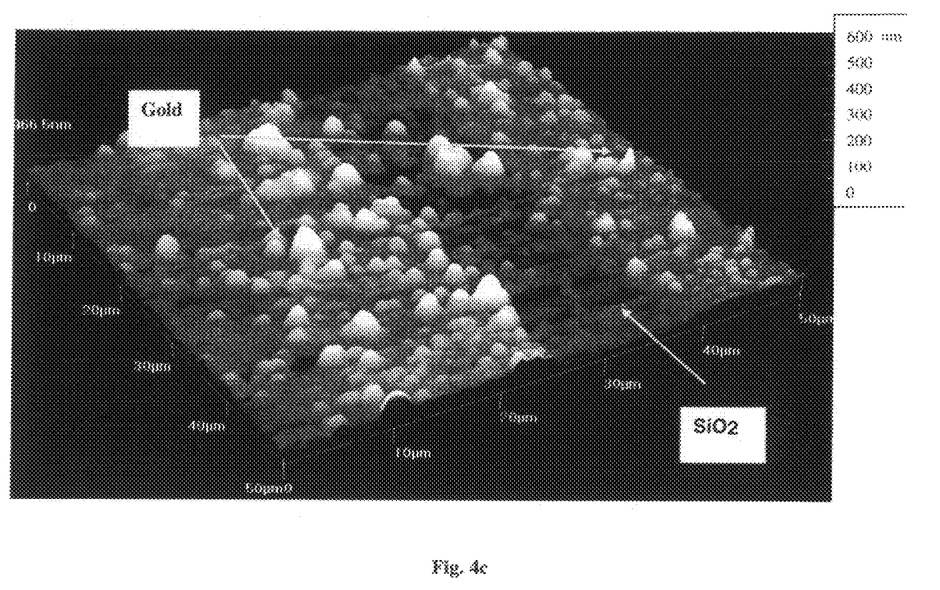

Atomic force microscopy (AFM) may be used to microscopically determine the distribution and homogeneity of the polyamine or polyamine functionalized coating, which is deposited onto the microelectrode array. FIG. 4 A depicts a photomicrograph of an AFM image of a bare microelectrode array surface, including bare silicon dioxide and bare gold surfaces. While FIGS. 4 B and 4 C, respectively, depict AFM images of trimethoxysilyl-ethylenediamine adsorbed on the silicon dioxide section of the microelectrode array's and semiconductor's surfaces and 3-aminopropyl functionalized silica gel adsorbed on the silicon dioxide and gold surfaces of the microelectrode array. In particular, FIG. 4 C illustrates that the silica gel is distributed evenly across both the silicon dioxide and gold surface; thus, facilitating accurate measurement of electrical characteristics of the polyamine or polyamine functionalized coating.

Figure 5:
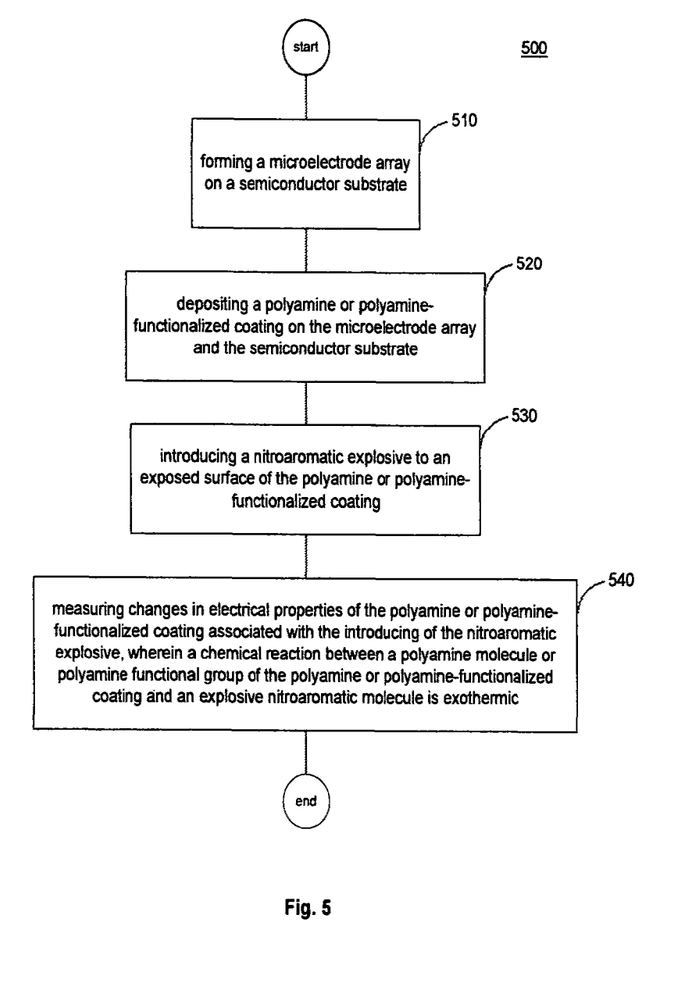
FIG. 5 illustrates a flowchart of an exemplary method for detecting a nitroaromatic explosive in an exemplary embodiment of the present invention.

FIG. 5 illustrates a flowchart of an exemplary method for detecting a nitroaromatic explosive of the present invention 500. The method comprises: forming a microelectrode array on a semiconductor substrate 510; depositing a polyamine or polyamine-functionalized coating on the microelectrode array and the semiconductor substrate 520; introducing a nitroaromatic explosive to an exposed surface of the polyamine or polyamine-functionalized coating 530; and measuring changes in electrical properties of the polyamine or polyamine-functionalized coating associated with the introducing of the nitroaromatic explosive, where a chemical reaction between a polyamine molecule or polyamine functional group of the polyamine or polyamine-functionalized coating and an explosive nitroaromatic molecule is exothermic 540.

Figure 6:
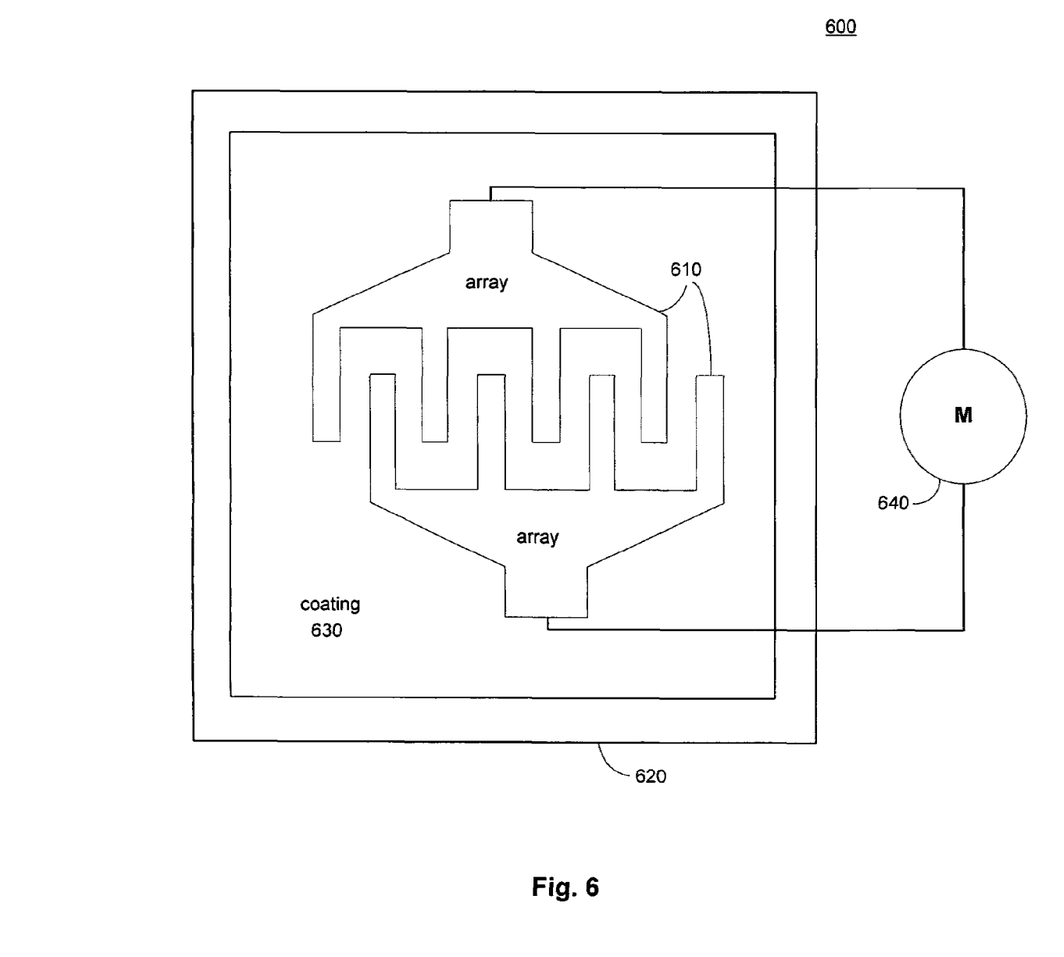
FIG. 6 illustrates a block diagram of an exemplary nitroaromatic explosive detector in an exemplary embodiment of the present invention.

FIG. 6 illustrates a block diagram of an exemplary nitroaromatic explosive detector 600 of the present invention that comprises a microelectrode array 610 formed on a semiconductor substrate 620; a polyamine or polyamine-functionalized coating 630 deposited on and contiguous with the microelectrode array 610 and the semiconductor substrate 620, where the polyamine or polyamine-functionalized coating includes an exposed surface upon which the nitroaromatic explosive is adsorbed; and a measuring device 640 for measuring any of resistance, conductance, and capacitance across the microelectrode array 610 to detect the nitroaromatic explosive, where a chemical reaction between a polyamine molecule or polyamine functional group of the polyamine or polyamine-functionalized coating and a nitroaromatic molecule of the nitroaromatic explosive is exothermic.

The polyamine or polyamine functionalized coating may also be used by sensors that detect physical changes other than electrical resistance, conductance, and capacitance in a microelectrode array to detect a nitroaromatic explosive. For example, a surface acoustic wave (SAW) sensor, as is well known in the art of micro-analyte detection, generates a surface acoustic wave confined to the surface of a piezoelectric substrate to which a polyamine or polyamine functionalized coating may be applied. The exothermic chemical reaction of a nitroaromatic explosive molecule with the polyamine or polyamine functionalized coating may result in changes to any of amplitude, phase, and harmonic content of the surface acoustic wave for detecting the nitroaromatic explosive. Similarly, surface plasmon resonance (SPR), which is used to measure adsorption of micro- or nano-analytes onto a planar metal surface, for example, gold or silver, may be used to detect a nitroaromatic explosive molecule that exothermically reacts with a polyamine or polyamine functionalized coating, which is contiguous with the planar metal surface, by spectroscopic measurements as is well know in the art. Similarly, microelectromechanical systems (MEMS), for example, a microfabricated nanomechanical cantilever sensor, may use a polyamine or polyamine functionalized coating of the cantilever beam to detect a nitroaromatic explosive molecule's exothermic reaction with the polyamine or polyamine functionalized coating by detecting stresses, as is well known in the art, induced between the polyamine or polyamine functionalized coating and the cantilever beam by the energetic reaction between the nitroaromatic explosive molecule and the polyamine molecule or polyamine function group of the polyamine or polyamine functionalized coating.

Because many varying and different exemplary embodiments may be made with the scope of the inventive concepts taught herein, and because many modifications may be made in the exemplary embodiments detailed herein in accordance with the descriptive requirements of the law, it is to be understood that the detailed descriptions herein are to be interpreted as illustrative and not in a limiting sense.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed:

1. A method for detecting a nitroaromatic explosive, the method comprising:
    forming a microelectrode array on a semiconductor substrate;
    depositing a polyamine or polyamine-functionalized coating on the microelectrode array and the semiconductor substrate;
    introducing a nitroaromatic explosive to an exposed surface of the polyamine or polyamine-functionalized coating; and
    measuring changes in electrical properties of the polyamine or polyamine-functionalized coating associated with the introducing of the nitroaromatic explosive, wherein a chemical reaction between a polyamine molecule or polyamine functional group of the polyamine or polyamine-functionalized coating and an explosive nitroaromatic molecule is exothermic.

2. The method of claim 1, wherein the depositing of the polyamine or polyamine-functionalized coating on the microelectrode array and the semiconductor substrate comprises vapor deposition of the polyamine or polyamine-functionalized coating.

3. The method of claim 1, wherein the depositing of the polyamine-functionalized coating on the microelectrode array and the semiconductor substrate comprises depositing a polyamine-functionalized silica-gel.

4. The method of claim 1, wherein the polyamine coating comprises any of diethylenetriamine (DETA), N-(3-aminopropyl)-1,3-propanediamine, ethylenediamine, 1,3-diaminopropane, 1,4-diaminobutane, 1,5-diaminopentane, 1,12- dodecanediamine (Spermine), hexamethylenediamine, bis(hexamethylene)triamine, N,N'-diethylethylenediamine, tris(2-aminoethyl)amine, N,N-diethylethylenediamine, diethylenetriaminepentaacetate (DTPA), [3-(2-aminoethylamino)propyl]trimethoxysilane, and 3-[2-(2-aminoethylamino)ethylamino]propyl-trimethoxysilane.

5. The method of claim 1, wherein the polyamine-functionalized coating comprises any of 3-(diethylenetriamino)propyl-functionalized silica, 3-(ethylenediamino)propyl-functionalized silica, and 3-aminopropyl-functionalized silica.

6. The method of claim 1, wherein the introducing of a nitroaromatic explosive comprises introducing any of 2,4-dinitrotoluene (2,4-DNT), 2-methyl-1,3,5-trinitrobenzene (TNT), 2,4,6-trinitrophenyl-N-methlynitramine (Tetryl), 1,3,5-trinitro-2-[2-(2,4,6-trinitrophenyl)ethenyl]benzene (HNS), 2,4,6-trinitrophenol (picric acid) and its salts, 1,3,5-triazido-2,4,6-trinitrobenzene (TNB), 1,3,5-triamino-2,4,6-trinitrobenzene (TATB), 2,4,6-trinitroaniline (TNA), 2,4,6 trinitro-1,3 benzenediamine (DATB), and 2-diazo-4,6-dinitrophenol (DDNP).

7. The method of claim 1, wherein the measuring changes in electrical properties of the polyamine or polyamine-functionalized coating comprises measuring any of resistance, conductance, and capacitance across the microelectrode array.

8. A nitroaromatic explosive detector, comprising:
a microelectrode array formed on a semiconductor substrate;
a polyamine or polyamine-functionalized coating deposited on and contiguous with the microelectrode array and the semiconductor substrate,
wherein the polyamine or polyamine-functionalized coating includes an exposed surface upon which the nitroaromatic explosive is adsorbed; and
a measuring device for measuring any of resistance, conductance, and capacitance across the microelectrode array to detect the nitroaromatic explosive,
wherein a chemical reaction between a polyamine or polyamine functional group molecule of the polyamine or polyamine-functionalized coating and an explosive nitroaromatic molecule is exothermic.

9. The nitroaromatic explosive detector of claim 8, wherein the polyamine or polyamine functionalized coating on the microelectrode array and the semiconductor substrate is vapor deposited to a thickness from about 1 nm to about 100,000 nm.

10. The nitroaromatic explosive detector of claim 8, wherein the polyamine-functionalized coating on the microelectrode array and the semiconductor substrate comprises a polyamine-functionalized silica-gel deposited to a thickness from about 1 nm to about 100,000 nm.

11. The nitroaromatic explosive detector of claim 8, wherein the polyamine coating comprises any of diethylenetriamine (DETA), N-(3-aminopropyl)-1,3-propanediamine, ethylenediamine, 1,3-diaminopropane, 1,4-diaminobutane, 1,5-diaminopentane, 1,12-dodecanediamine (Spermine), hexamethylenediamine, bis(hexamethylene)triamine, N,N'-diethylethylenediamine, tris(2-aminoethyl)amine, N,N-diethylethylenediamine, diethylenetriaminepentaacetate (DTPA), [3-(2-aminoethylamino)propyl]trimethoxysilane, and 3-[2-(2-aminoethylamino)ethylamino]propyl-trimethoxysilane.

12. The nitoaromatic explosive detector of claim 8, wherein the polyamine-functionalized coating comprises any of 3-(diethylenetriamino)propyl-functionalized silica, 3-(ethylenediamino)propyl-functionalized silica, and 3-aminopropyl-functionalized silica.

13. The nitroaromatic explosive detector of claim 8, wherein the nitroaromatic explosive comprises any of 2,4-dinitrotoluene (2,4-DNT), 2-methyl-1,3,5-trinitrobenzene (TNT), 2,4,6-trinitrophenyl-N-methlynitramine (Tetryl), 1,3,5-trinitro-2-[2-(2,4,6-trinitrophenyl)ethenyl]benzene (HNS), 2,4,6-trinitrophenol (picric acid) and its salts, 1,3,5-triazido-2,4,6-trinitrobenzene (TNB), 1,3,5-triamino-2,4,6-trinitrobenzene (TATB), 2,4,6-trinitroaniline (TNA), 2,4,6 trinitro-1,3 benzenediamine (DATB), and 2-diazo-4,6-Dinitrophenol (DDNP).

14. The nitroaromatic explosive detector of claim 8, wherein the microelectrode array comprises any of silver, gold, platinum, palladium, nickel, chromium, copper, iron, tungsten, titanium, zinc, manganese, tantalum, and aluminum.

15. The nitroaromatic explosive detector of claim 8, wherein the semiconductor substrate comprises any of silicon, indium nitride, silicon dioxide, germanium, gallium arsenide, gallium nitride, silicon carbide, and silicon nitride.

16. The nitroaromatic explosive detector of claim 8, wherein the measuring device for measuring any of resistance, conductance, and capacitance further comprises a direct current power supply and a time-varying power supply.

* * * * *